United States Patent

Ozeki et al.

Patent Number: 5,252,589
Date of Patent: Oct. 12, 1993

[54] BENZOCYCLOHEPTENE DERIVATIVE AND PROCESS FOR PREPARATION THEREOF

[75] Inventors: Masakatsu Ozeki, Kawagoe; Kōsuke Yasuda, Kounosu; Masamichi Morimoto, Tokyo; Tohru Ishizuka, Kitamoto; Kunio Nosaka, Kasukabe, all of Japan

[73] Assignee: Tanabe Seikayu Co., Ltd., Osaka, Japan

[21] Appl. No.: 990,239

[22] Filed: Dec. 14, 1992

[51] Int. Cl.$^5$ .................. A61K 31/38; A61K 31/445
[52] U.S. Cl. ........................ 514/319; 514/422; 514/231.5; 546/206; 548/527; 544/146
[58] Field of Search ............... 546/206; 548/527; 514/319, 231.5, 422; 544/146

[56] References Cited

U.S. PATENT DOCUMENTS 4,091,115  5/1978  Nedelec et al.
4,777,176 10/1988  Worthington et al. ............ 514/319

OTHER PUBLICATIONS

Chemical Abstracts, vol. 62, 11751b (1965).
Thies et al., J. Org. Chem., vol. 45, pp. 185–187 (1980).
Wong et al., J. Med. Chem. vol. 27, pp. 20–27 (1984).
Jones et al., J. Chem. Soc., (C), pp. 2176–2181 (1969).

Primary Examiner—Marianne M. Cintins
Assistant Examiner—John Peabody
Attorney, Agent, or Firm—Birch, Stewart, Kolasch & Birch

[57] ABSTRACT

There is disclosed a benzocycloheptene compound of the formula:

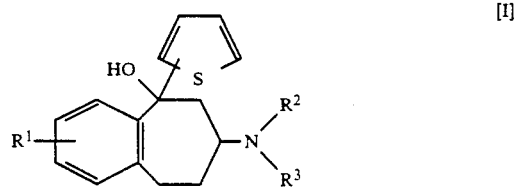

[I]

wherein $R^1$ is hydrogen atom, a halogen atom or a lower alkoxy group, $R^2$ and $R^3$ are independently selected from hydrogen atom, a lower alkyl group and a lower alkenyl group, or $R^2$ and $R^3$ combine together with adjacent nitrogen atom to form a heteromonocyclic group, or a pharmaceutically acceptable salt thereof, which has an excellent inhibitory activity against contraction of urinary bladder.

9 Claims, No Drawings

BENZOCYCLOHEPTENE DERIVATIVE AND PROCESS FOR PREPARATION THEREOF

FIELD OF THE INVENTION

This invention relates to a benzocycloheptene derivative and processes for preparation thereof.

BACKGROUND OF THE INVENTION

A patient with pollakiuria micturates more frequently than a healthy person and therefore, pollakiuria causes the patient much trouble in his life. Since micturition is caused by reflective contraction of urinary bladder, a drug which inhibits the reflective contraction is useful for treatment of pollakiuria. Drugs such as Flavoxate hydrochloride [chemical name: 3-methyl-4-oxo-2-phenyl-4H-1-benzopyran-8-carboxylic acid 2-piperidinoethyl ester.hydrochloride] and Oxybutynin hydrochloride [chemical name: α-cyclohexyl-α-hydroxy-benzeneacetic acid 4-(diethylamino)-2-butynyl ester.hydrochloride] have been known as drugs for prophylaxis and treatment of pollakiuria based on the above-identified activity (The MERCK INDEX tenth edition, page 587 and 997). On the other hand, Japanese Patent Publication (unexamined) No. 17455 of 1977 and U.S. Pat. No. 4,091,115 disclose 6,7,8,9-tetrahydro-5-phenyl-7-methylamino-5H-benzocyclohepten-5-ol and its 7-dimethylamino compound as intermediate compounds of antidepressant agent. However, any pharmaceutical activity of said compounds has not been known.

SUMMARY OF THE INVENTION

As a result of various investigations, the inventors of the present invention have found a novel pharmaceutical compound having a potent inhibitory activity against the contraction of the urinary bladder.

Thus, an object of the present invention is to provide a novel benzocycloheptene derivative which is useful for prophylaxis and therapeutic treatment of pollakiuria, nocturia, enuresis or irritable bladder.

Another object is to provide a novel pharmaceutical composition useful for prophylaxis and therapeutic treatment of pollakiuria, nocturia, enuresis or irritable bladder, which contains said benzocycloheptene derivative as the therapeutically active ingredient. And still another object is to provide processes for preparing said novel benzocycloheptene derivative. These and other objects and advantages of the invention will be apparent to those skilled in the art from the following description.

DETAILED DESCRIPTION OF THE INVENTION

This invention relates to a benzocycloheptene derivative of the following formula [I]:

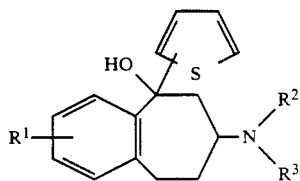

wherein $R^1$ is hydrogen atom, a halogen atom or a lower alkoxy group, $R^2$ and $R^3$ are independently selected from hydrogen atom, a lower alkyl group and a lower alkenyl group, or $R^2$ and $R^3$ combine together with adjacent nitrogen atom to form a heteromonocyclic group, or a pharmaceutically acceptable salt thereof.

Examples of the benzocycloheptene derivative of the present invention include those of the formula [I] in which $R^1$ is hydrogen atom, a halogen atom such as chlorine atom, bromine atom or fluorine atom or a lower alkoxy group, $R^2$ and $R^3$ are independently selected from hydrogen atom, a lower alkyl group and a lower alkenyl group, or $R^2$ and $R^3$ combine together with adjacent nitrogen atom to form a heteromonocyclic group such as piperidinyl group, pyrrolidinyl group or morpholinyl group.

Among these derivatives, pharmaceutically preferred examples of the compounds are those of the formula [I] wherein the thienyl group substituted at 5-position of the benzocycloheptene ring is 2-thienyl group, $R^1$ is substituted at 3-position of the benzocycloheptene ring, one of $R^2$ and $R^3$ is hydrogen atom or a lower alkyl group and the other is a lower alkyl group or a lower alkenyl group, or $R^2$ and $R^3$ combine together with adjacent nitrogen atom to form piperidinyl group or pyrrolidinyl group.

Pharmaceutically more preferred examples of the compounds are those of the formula [I] wherein $R^1$ is hydrogen atom, one of $R^2$ and $R^3$ is hydrogen atom or a lower alkyl group and the other is a lower alkyl group, or $R^2$ and $R^3$ combine together with adjacent nitrogen atom to form piperidinyl group or pyrrolidinyl group.

The compound [I] of the present invention may exist in the form of two stereoisomers (i.e., cis and trans isomers) or four optically active isomers (i.e., (+)-cis, (−)-cis, (+)-trans, (−)-trans isomers) due to two asymmetric carbon atoms, and this invention includes all of these isomers and a mixture thereof. Among said isomers, however, the cis isomer, especially the (+)-cis isomer is preferred for medicinal use.

The compound [I] of the present invention may be used as a medicament either in the free form or a pharmaceutically acceptable salt. Examples of the pharmaceutically acceptable salt include an inorganic acid addition salt such as hydrochloride, hydrobromide, sulfate and the like, and an organic salt addition salt such as acetate, oxalate, fumarate, maleate, tartrate, benzenesulfonate and the like.

The compound [I] or a pharmaceutically acceptable salt thereof may be administered either orally or parenterally to a warm-blooded animal including human being and may also be used in the form of a pharmaceutical preparation containing the same compound in admixture with pharmaceutical excipients suitable for oral or parenteral administration (such as conventional pharmaceutically acceptable carriers or diluents). The pharmaceutical preparations may be in solid form such as tablets, capsules and powders, or in liquid form such as solutions, suspensions or emulsions. Further, when administered parenterally, it may be used in the form of injections.

The daily dose of the compound [I] of the present invention or a pharmaceutically acceptable salt thereof may vary depending on administration route, the age, weight and conditions of the patient, and kinds of the diseases to be treated, but it is usually in the range of about 0.01 to 10 mg/kg of body weight in the case of oral administration and it is usually in the range of 0.001 to 1 mg/kg of body weight in the case of parenteral administration.

Moreover, the compound [I] of the present invention and pharmaceutically acceptable salts thereof are low in toxicity, and hence, they show high safety as a medicament. For example, when (±)-cis-5-(2-thienyl)-7-isopropylamino-6,7,8,9-tetrahydro-5H-benzocyclohepten-5-ol was orally administered to mice at a dose of 500 mg/kg, no mouse died two days after the administration thereof.

As mentioned hereinbefore, the benzocycloheptene derivative [I] and a pharmaceutically acceptable salt thereof have a potent inhibitory activity against the contraction of urinary bladder. Therefore, the compound [I] and a pharmaceutically acceptable salt thereof are useful for treatment and/or prophylaxis of urinary system diseases associated with contracting function disorder of urinary bladder or ureter, for example, pollakiuria (frequent micturition), nocturia (voiding during the night), enuresis (bed-wetting at night), irritable bladder and the like.

According to this invention, the compound [I] may be prepared by treating a carbonyl compound of the formula [II]:

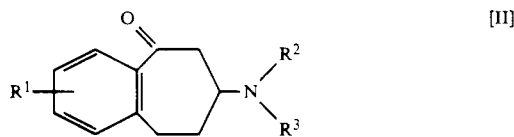

wherein $R^1$, $R^2$ and $R^3$ are the same as defined above, or a salt thereof with a thiophen compound of the formula [III]:

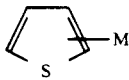

wherein M is an alkali metal or a group of the formula: -MgX in which X is a halogen atom.

Among the compound [I] of the present invention, the compound of the formula [I-a]:

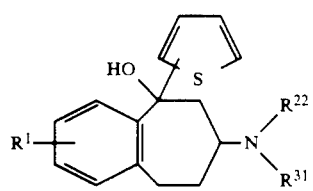

wherein $R^{22}$ is hydrogen atom, a lower alkyl group or a lower alkenyl group, $R^{31}$ is a lower alkyl group or a lower alkenyl group and $R^1$ is the same as defined above, may be also prepared by subjecting a compound [I-b]:

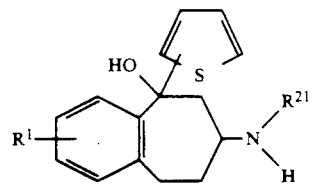

wherein $R^{21}$ is hydrogen atom, a lower alkyl group or a lower alkenyl group and $R^1$ is the same as defined above to N-alkylation or N-alkenylation.

The reaction of the carbonyl compound [II] with the thiophen compound [III] may be carried out in the presence or absence of a Lewis acid in a solvent. Examples of the alkali metal which is shown by M in the compound [III] include lithium and the like and examples of the group of the formula: -MgX which is shown by M in the compound [III] include -MgBr, -MgI and the like. The starting compound [II] may be used for the above-mentioned reaction in the form of either free base or a salt thereof. Examples of the salt include either an organic acid addition salt or an inorganic acid addition salt. Example of the Lewis acid includes tin(IV) chloride, trimethylaluminum, t-butoxydimethylaluminum and the like. The solvent is not particularly limited so long as it is inactive in the reactions, but may include, for example, ethers such as diethyl ether or tetrahydrofuran and toluene or a solvent mixture thereof. The reaction of the carbonyl compound [II] with the thiophen compound [III] may be carried out under cooling or at room temperature, for example, at a temperature of −78° C. to 25° C. When the above-mentioned reaction is carried out in the presence of the Lewis acid, a cis isomer of the compound [I] is obtained as the main product and when carried out in the absence of the Lewis acid, a trans isomer of the compound [II] is obtained as the main product.

The N-alkylating or N-alkenylating reaction of the compound [I-b] may be carried out in a conventional manner, for example, by reacting the compound [I-b] with an alkylating agent or an alkenylating agent in the presence or absence of an acid acceptor in a suitable solvent or without a solvent. Examples of the alkylating agent include a lower alkyl halide, a lower alkyl methanesulfonate, a lower alkyl toluenesulfonate, a lower alkyl sulfate and the like, and examples of the alkenylating agent include a lower alkenyl halide and the like. Examples of the acid acceptor include an alkali metal hydroxide (e.g., sodium hydroxide, potassium hydroxide), an alkali metal hydride (e.g., sodium hydride), an alkali metal alkoxide(e.g., sodium methoxide, sodium ethoxide, potassium t-butoxide), an alkali metal carbonate (e.g., sodium carbonate), an alkali metal bicarbonate (e.g., sodium bicarbonate), an organic amine (e.g., triethylamine, diisopropylethylamine, pyridine, N, N-dimethylaminopyridine), an alkali metal (e.g., sodium) and an alkali metal amide substituted by a lower alkyl group (e.g., lithium diisopropylamide). Ethers such as diethyl ether, tetrahydrofuran, dioxane or dimethoxyethane, ketones such as acetone or 2-butanone, N, N-dimethylformamide, dimethylsulfoxide, chloroform and methylene chloride are preferably used as the solvent. The reaction is carried out under cooling, at room temperature or with heating, preferably at a temperature of 0° C. to 70° C.

Besides, when the starting compound [I-b] in which $R^{21}$ is hydrogen atom is used in the above-mentioned reaction, 7-mono-alkyl (or mono-alkenyl)amino compound or 7-di-alkyl (or di-alkenyl)amino compound can be obtained selectively by adjusting the amount of the alkylating or alkenylating agent.

The N-alkylating reaction of the compound [I-b] may also be carried out by a reductive alkylation. The said reductive alkylation may be carried out in a conventional manner by reacting the compound [I-b] with an aldehyde or its acetal of the formula:

$$R^4\text{-CHO}$$

wherein $R^4$ is hydrogen atom or an alkyl group which has less one carbon atom than $R^{31}$, in a suitable solvent and then reducing the obtained product (i.e., schiff base) with a reducing agent. Examples of an aldehyde include a lower alkyl aldehyde such as formaldehyde, acetaldehyde and the like. Examples of the reducing agent include an alkali metal borohydride such as sodium borohydride, lithium borohydride, an alkali metal cyanoborohydride and the like. Methanol, ethanol and t-butanol are preferably used as the solvent. The reaction is carried out under cooling or at room temperature, preferably at a temperature of $-10°$ C. to $25°$ C.

If required, the racemic mixture of the compound [I] can be resolved into each optically active enantiomers thereof. Example of the resolving agent includes conventional resolving agents, for example, optically active mandelic acid, optically active dibenzoyltartaric acid, optically active N-acetylphenylalanine and the like. For example, the optical resolution of ($\pm$)-trans-3-fluoro-5-(2-thienyl)-7-diethylamino-6,7,8,9-tetrahydro-5H-benzocyclohepten-5-ol can be carried out by the steps of reacting the said compound with (S)-(+)-mandelic acid and filtrating the precipitate to give (+)-isomer thereof. The mother liquor which is obtained after isolating (+)-isomer is treated with (R)-(−)-mandelic acid to give (−) -isomer.

Concomitantly, the starting compound [II] of the present invention can be prepared, for example, from a compound of the formula [IV]:

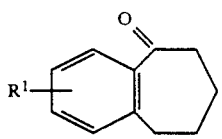

wherein R1 is the same as defined above, according to the method described in Japanese Patent Publication (unexamined) No. 17455 of 1977.

Throughout the specification and claims, the term "lower alkyl group", "lower alkoxy group" and "lower alkenyl group" should be referred to as an alkyl group of 1 to 6, preferably 1 to 4 carbon atoms, an alkoxy group of 1 to 6, preferably 2 to 4 carbon atoms and an alkenyl group of 2 to 6, preferably 2 to 4 carbon atoms, respectively.

EXPERIMENT (Inhibitory effect on urinary bladder contractions)

Rats (body weight: 250 to 450 g) were used as the test animals. The urinary bladder was isolated and suspended vertically in Tyrode solution aerated with a gas mixture of 95% $O_2$ and 5% $CO_2$ at 37° C. Urinary bladder was filled with 0.8 ml of a physiological saline solution. An ureteral catheter was inserted into the urinary bladder and one end of the catheter was connected to a pressure transducer. The change in intravesical pressure of the bladder was recorded. Contraction was induced by adding $1 \times 10^{-5}$M carbachol at 30 minutes intervals. After the contraction became stable, the test compound was added to the Tyrode solution 5 minutes before the addition of carbachol. The inhibitory effect of the test compound on the contraction was expressed as $IC_{50}$, i.e., the concentration of the test compound which was required to induce 50% inhibition of the pressure obtained just before addition of carbachol. The results are shown in Table 1.

TABLE 1

| Test Compounds | $IC_{50}$ ($\mu$M) |
| --- | --- |
| ($\pm$)-cis-5-(2-thienyl)-7-isopropylamino-6,7,8,9-tetrahydro-5H-benzocyclohepten-5-ol | 2.6 |
| ($\pm$)-cis-5-(2-thienyl)-7-isopropylamino-6,7,8,9-tetrahydro-5H-benzocyclohepten-5-ol | 2.2 |
| ($\pm$)-cis-5-(2-thienyl)-7-diethylamino-6,7,8,9-tetrahydro-5H-benzocyclohepten-5-ol | 1.1 |
| ($\pm$)-cis-5-(2-thienyl)-7-(1-piperidinyl)-6,7,8,9-tetrahydro-5H-benzocyclohepten-5-ol | 0.7 |

EXAMPLE 1

(1) 27 ml of 0.714M 2-thienyl lithium solution (solvent; n-hexane:ether=1:1) are added dropwise to a solution of 1.46 g of 7-diethylamino-6,7,8,9-tetrahydro-5H-benzocyclohepten-5-one in 15 ml of ether under ice-cooling for 15 minutes and the mixture is stirred under ice-cooling during 20 minutes. An aqueous saturated sodium bicarbonate solution is added thereto and extracted with ethyl acetate. The ethyl acetate layer is washed, dried and evaporated to remove the solvent. The residue is subjected to silica gel column chromatography (solvent; chloroform:methanol=30:1, containing a small amount of aqueous concentrated ammonium hydroxide solution) and the first eluate is evaporated to remove the solvent, and the residue is recrystallized from n-hexane to obtain 0.29 g of cis-5-(2-thienyl)-7-diethylamino-6,7,8,9-tetrahydro-5H-benzocyclohepten-5-ol as crystal.

Yield: 14.4% m.p.: 85.5°–88° C.

½ Fumarate of the product:

m.p.: 168°–170° C. (recrystallized from ethanol)

The subsequent eluate is condensed to obtain 1.27 g of trans-5-(2-thienyl)-7-diethylamino-6,7,8,9-tetrahydro-5H-benzocyclohepten-5-ol as an oil.

Yield: 63.8%

½ Fumarate of the product:

m.p.: 196.5°–198.5° C. (dec.) (recrystallized from ethanol)

EXAMPLES 2 TO 5

The corresponding starting compounds are treated in the same manner as described in Example 1 to obtain the compounds listed in Table 2.

TABLE 2

| Ex Nos. | R¹ | –N(R²)(R³) | trans/cis | salt | m.p.(°C.) (Recrystallization Solvent) |
|---|---|---|---|---|---|
| 2 | —F | —N(CH₃)₂ | trans | ½Fumarate | 192–194(dec.)(Isopropanol-Ether) |
| 3 | —F | —N(C₂H₅)₂ | cis | — | 117–120(dec.)(n-Hexane) |
|   | —F | —N(C₂H₅)₂ | trans | ½Fumarate | 198–199(dec.)(Isopropanol-Ether) |
| 4 | —OCH₃ | —N(C₂H₅)₂ | cis | — | 105–109(n-Hexane) |
|   | —OCH₃ | —N(C₂H₅)₂ | trans | ½Fumarate | 194–197(Ethanol) |
| 5 | —F | —N(piperidinyl) | cis | ½Fumarate | 206.5–207.5(dec.)(Ethanol) |
|   | —F | —N(piperidinyl) | trans | Oxalate | 89.5–92.0(dec.)(Ethanol) |

EXAMPLE 6

A solution of 9.7 ml of n-butyl lithium in n-hexane is added to a stirred solution of 1.31 ml of thiophen in 20 ml of tetrahydrofuran at −45° C. The mixture is stirred at a temperature from −20° C. to −30° C. for 1 hour. A solution of 2.05 g of 6,7,8,9-tetrahydro-7-(1-piperidinyl)-5H-benzocyclohepten-5-one in 15 ml of tetrahydrofuran is added dropwise thereto at −65° C. and the mixture is allowed to warm to a temperature of 5° C. An aqueous saturated sodium bicarbonate solution is added to the reaction mixture and the mixture is extracted with ethyl acetate. The ethyl acetate layer is washed, dried and evaporated to remove the solvent. The residue is purified by silica gel column chromatography (solvent; chloroform:methanol=20:1, containing a small amount of aqueous concentrated ammonium hydroxide solution) to obtain 1.93 g of trans-5-(2-thienyl)-7-(1-piperidinyl)-6,7,8,9-tetrahydro-5H-benzocyclohepten-5-ol as crystal.

Yield: 70% m.p.: 88°–89° C. (recrystallized from isopropyl ether)

Fumarate of the product:

m.p.: 166°–167° C. (recrystallized from a mixture of ethanol and ether)

EXAMPLE 7

A solution of 0.414 ml of tin(IV) chloride in 10 ml of toluene is cooled to −65° C. and a solution of 0.802 g of 7-tert-butylamino-6,7,8,9-tetrahydro-5H-benzocyclohepten-5-one in 10 ml of toluene is added dropwise thereto under argon atmosphere during 40 minutes. The mixture is stirred at −65° C. for 1.3 hours. 13 ml of 1.07M 2-thienyl lithium solution (solvent; toluene:ether=10:3) are added dropwise thereto during 20 minutes and the mixture is stirred at −65° C. for 30 minutes. An aqueous saturated sodium bicarbonate solution is added thereto and methanol are further added thereto, and the mixture is stirred at room temperature. Insoluble materials are filtered off and the filtrate is extracted with ethyl acetate. The ethyl acetate layer is washed, dried and evaporated to remove the solvent. The residue is purified by silica gel column chromatography (solvent; chloroform:methanol=15:1, containing a small amount of an aqueous concentrated ammonium hydroxide solution) to obtain 0.824 g of cis-5-(2-thienyl)-7-tert-butylamino-6,7,8,9-tetrahydro-5H-benzocyclohepten-5-ol as an oil.

Yield: 75%

Fumarate of the product:

m.p.: 177°–178.5° C. (dec.) (recrystallized from a mixture of ethanol and ether)

EXAMPLES 8 TO 13

The corresponding starting compounds are treated in the same manner as described in Example 7 to obtain the compounds listed in Table 3.

TABLE 3

[Structure: benzocycloheptene with HO, thienyl (S), R¹ on benzene ring, NR²R³ on cycloheptene]

| Ex Nos. | R¹ | -N(R²)(R³) | trans/cis | salt | m.p.(°C.) (Recrystallization Solvent) |
|---|---|---|---|---|---|
| 8 | —H | —N(CH₃)₂ | cis | ½Fumarate | 203-204(dec.)(Methanol-Ether) |
|   | —H | —N(CH₃)₂ | trans | Fumarate | 166-167(dec.)(Ethanol-Ether) |
| 9 | —F | —NHC(CH₃)₃ | cis | Fumarate | 186-190(dec.)(Ethanol-Ether) |
| 10 | —F | —N(CH₃)₂ | cis | ½Fumarate | 188-189(dec.)(Isopropanol-Ether) |
| 11 | —H | —N(piperidinyl) | cis | ½Fumarate | 191-192(dec.)(Ethanol) |
| 12 | —H | —N(pyrrolidinyl) | cis | ½Fumarate | 210-212(dec.)(Methanol-Ether) |
| 13 | —OCH₃ | —N(piperidinyl) | cis | ½Fumarate | 217-219(dec.)(Ethanol) |

EXAMPLE 14

A solution of 1.02 g of tert-butyl alcohol in 10 ml of toluene is added dropwise to a mixture of 6.90 ml of 2.0M trimethylaluminum solution (solvent; n-hexane) and 20 ml of toluene under argon atmosphere at a temperature from 5° to 10° C. during 10 minutes. The mixture is stirred at the same temperature for 30 minutes and then cooled to −65° C. A solution of 3.0 g of 7-isopropylamino-6,7,8,9-tetrahydro-5H-benzocyclohepten-5-one in 30 ml of toluene is added dropwise thereto during 10 minutes and the mixture is stirred for 40 minutes. 65 ml of 0.64M 2-thienyl lithium solution (solvent; toluene:ether=10:3) are added dropwise thereto at −60° C. for 30 minutes and the mixture is stirred at the same temperature for 30 minutes. Methanol and then an aqueous saturated sodium bicarbonate solution are added thereto and the mixture is extracted with ethyl acetate. The ethyl acetate layer is washed, dried and evaporated to remove the solvent. The residue is purified by silica gel column chromatography (solvent; chloroform:methanol=20:1, containing a small amount of aqueous concentrated ammonium hydroxide solution) and the eluate is evaporated to remove the solvent, and the residue is recrystallized from a mixture of isopropyl ether and n-hexane to obtain 2.25 g of cis-5-(2-thienyl)-7-isopropylamino-6,7,8,9-tetrahydro-5H-benzocyclohepten-5-ol as crystal.

Yield: 54.2%
m.p.: 121°-123° C.

½ Fumarate of the product:
m.p.: 228.5°-230.5° C. (dec.) (recrystallized from a mixture of methanol and ether)

EXAMPLE 15

(1)-(a) 3.15 g of (±)-cis-5-(2-thienyl)-7-tert-butylamino-6,7,8,9-tetrahydro-5H-benzocyclohepten-5-ol and 3.76 g of (−)-L-dibenzoyltartaric acid are dissolved in acetone under heating. After cooling, the precipitated crystals are recrystallized from isopropyl alcohol to obtain 2.08 g of (+)-cis-5-(2-thienyl)-7-tert-butylamino-6,7,8,9-tetrahydro-5-H-benzocyclohepten-5-ol.½(−)-L-dibenzoyltartrate.

Yield: 38.0%
m.p.: 152.5°-155.5° C. (dec.)

(1)-(b) The above-obtained product is dissolved in a mixture of ether and an aqueous sodium bicarbonate solution, and the ether layer is washed, dried and evaporated to remove the solvent. The residue is recrystallized from n-hexane to obtain 0.943 g of (+)-cis-5-(2-thienyl)-7-tert-butylamino-6,7,8,9-tetrahydro-5H-benzocyclohepten-5-ol.

m.p.: 79°-80.5° C.
$[\alpha]_D^{20}$: +74.1° (c=1.0, chloroform)

(1)-(c) 0.828 g of the above-obtained product is converted to its fumarate and recrystallized from a mixture of ethanol and acetone to obtain 1.14 g of (+)-cis-5-(2-thienyl)-7-tert-butylamino-6,7,8,9-tetrahydro-5H-benzocyclohepten-5ol. fumarate as crystal.

m.p.: 164.5°-166° C. (dec.)
$[\alpha]_D^{20}$: +48.9° (c=1.0, methanol)

(2) A mixture of ether and an aqueous sodium bicarbonate solution is added to the mother liquor which is obtained after isolating (+)-cis-5-(2-thienyl)-7-tert-butylamino-6,7,8,9-tetrahydro-5H-benzocyclohepten-5-ol.(−)-L-dibenzoyltartrate. The organic layer is washed, dried and condensed. The residue and (+)-D-dibenzoyltartaric acid are treated in the same manner as described in Paragraph (1)-(a) and (b) to obtain 0.853 g of (−)-cis-5-(2-thienyl)-7-tert-butylamino-6,7,8,9-tetrahydro-5H-benzocyclohepten-5-ol as crystal.

m.p. : 79°-80.5° C.
$[\alpha]_D^{20}$ : −74.9° (c=1.0, chloroform)

Fumarate of the product:
m.p. : 168°-169° C. (dec.) (recrystallized from a mixture of ethanol and acetone)
$[\alpha]_D^{20}$ : −49.8° (c=1.0, methanol)

EXAMPLE 16

(1)-(a) 1.30 g of (±)-cis-5-(2-thienyl)-7-isopropylamino-6,7,8,9-tetrahydro-5H-benzocyclohepten-5-ol and 0.893 g of N-acetyl-D-phenylalanine are dissolved in ethanol, and a mixture of ethanol and ether is added thereto. The precipitated crystals are recrystallized from a mixture of ethanol and ether to obtain 0.693 g of (−)-cis-5-(2-thienyl)-7-isopropylamino-6,7,8,9-tetrahydro-5H-benzocyclohepten-5-ol.N-acetyl-D-phenylalanine salt.

Yield: 31.7%
m.p.: 193°-194.5° C. (dec.)
$[\alpha]_D^{20}$: −76.7° (c=1.0, methanol)

(1)-(b) The above-obtained product is treated in the same manner as described in example 15-(1)-(b) to obtain (−)-cis-5-(2-thienyl)-7-isopropylamino-6,7,8,9-tetrahydro-5H-benzocyclohepten-5-ol.

m.p.: 106.5°-107.5° C. (recrystallized from n-hexane)
$[\alpha]_D^{20}$: −74.6° (c=1.1, chloroform)

½ Fumarate of the product:
m.p.: 211.5°-212.5° C. (dec.) (recrystallized from a mixture of methanol and ether)
$[\alpha]_D^{20}$: −63.1° (c=0.50, methanol)

(2)-(a) A mixture of ethyl acetate and an aqueous sodium bicarbonate solution is added to the mother liquor which is obtained after isolating (−)-cis-5-(2-thienyl)-7-isopropylamino-6,7,8,9-tetrahydro-5H-benzocyclohepten-5-ol.N-acetyl-D-phenylalanine salt. The organic layer is washed, dried and condensed. The residue and 0.550 g of N-acetyl-L-phenylalanine are treated in the same manner as described in example 15-(1)-(a) to obtain 0.716 g of (+)-cis-5-(2-thienyl)-7-isopropylamino-6,7,8,9-tetrahydro-5H-benzocyclohepten-5-ol.N-acetyl-L-phenylalanine salt.

Yield: 32.7%
m.p.: 193°-194.5° C. (dec.)
$[\alpha]_D^{20}$: +77.7° (c=1.0, methanol)

(2)-(b) The above-obtained product is treated in the same manner as described in example 15-(1)-(b) to obtain (+)-cis-5-(2-thienyl)-7-isopropylamino-6,7,8,9-tetrahydro-5H-benzocyclohepten-5-ol.

m.p.: 107°-108° C. (recrystallized from n-hexane)
$[\alpha]_D^{20}$: +74.9° (c=1.1, chloroform)

½ Fumarate of the product:
m.p.: 211.5°-212.5° C. (dec.) (recrystallized from a mixture of methanol and ether)
$[\alpha]_D^{20}$: +63.2° (c=0.54, methanol)

EXAMPLE 17

(1)-(a) 4.15 g of (±)-trans-5-(2-thienyl)-7-diethylamino-6,7,8,9-tetrahydro-5H-benzocyclohepten-5-ol and 5.05 g of (2R, 3R)-3-{(5-chloro-2-nitrophenyl)thio}-2-hydroxy-3-(4-methoxyphenyl)propionic acid are dissolved in ethyl acetate, and a mixture of ethyl acetate and ether is added thereto. The precipitated crystals are recrystallized from ethanol twice to obtain 2.50 g of (+)-(5S, 7R)-trans-5-(2-thienyl)-7-diethylamino-6,7,8,9-tetrahydro-5H-benzocyclohepten-5-ol.(2R, 3R)-3-{(5-chloro-2'-nitrophenyl)thio}-2-hydroxy-3-(4-methoxyphenyl)propionate.

Yield: 27.1%
m.p.: 165.5°-166.5° C. (dec.)
$[\alpha]_D^{20}$: −15.4° (c=1.0, methanol)

(1)-(b) A mixture of 10% citric acid and ethyl acetate is added to the above-obtained product, and the mixture is stirred at room temperature for 3 hours. The aqueous layer is separated from the reaction mixture, and potassium carbonate is added thereto. The mixture is extracted with ethyl acetate. The ethyl acetate layer is washed, dried and evaporated to remove the solvent. The residue is purified by silica gel column chromatography (solvent; chloroform:methanol=20:1, containing a small amount of aqueous concentrated ammonium hydroxide solution) to obtain (+)-(5S,7R)-trans-5-(2-thienyl)-7-diethylamino-6,7,8,9-tetrahydro-5H-benzocyclohepten-5-ol as an oil.

$[\alpha]_D^{20}$: +64.0° (c=1.0, chloroform)

Fumarate of the product:
m.p.: 148.5°-149.5° C.
$[\alpha]_D^{20}$: +37.3° (c=1.0, methanol)

(2)-(a) A mixture of 10% citric acid and ethyl acetate is added to the mother liquor which is obtained after isolating (+)-(5S, 7R)-trans-5-(2-thienyl)-7-diethylamino-6,7,8,9-tetrahydro-5H-benzocyclohepten-5ol.(2R, 3R)-3-{(5-chloro-2-nitrophenyl)thio}-2-hydroxy-3-(4-methoxyphenyl)propionate, and the mixture is stirred at room temperature for 3 hours. The aqueous layer is separated from the reaction mixture, potassium carbonate is added thereto and the mixture is extracted with ethyl acetate. The ethyl acetate layer is washed, dried and evaporated to remove the solvent. The residue and 3.19 g of (2S, 3S)-3-{(5-chloro-2-nitrophenyl)thio}-2-hydroxy-3-(4-methoxyphenyl)propionic acid are treated in the same manner as described in example 15-(1)-(a) to obtain 2.10 g of (−)-trans-5-(2-thienyl)-7-diethylamino-6,7,8,9-tetrahydro-5H-benzocyclohepten-5-ol.(2S, 3S)-3-{(5-chloro-2-nitrophenyl)thio}-2-hydroxy-3-(4-methoxyphenyl)propionate.

Yield: 22.8%
m.p.: 164.5°-166° C. (dec.)
$[\alpha]_D^{20}$: +15.8° (c=1.0, methanol)

(2)-(b) The above-obtained product is treated in the same manner as described in paragraph (1)-(b) to obtain (−)-(5R, 7S)-trans-5-(2-thienyl)-7-diethylamino-6,7,8,9-tetrahydro-5H-benzocyclohepten-5-ol as an oil.

$[\alpha]_D^{20}$: −63.8° (c=1.0, chloroform)

Fumarate of the product:
m.p.: 145.0°-146.5° C. (recrystallized from isopropanol)

$[\alpha]_D^{20}$: $-37.7°$ (c=1.0, methanol)

EXAMPLE 18

(1)-(a) 59 g of (±)-trans-3-fluoro-5-(2-thienyl)-7-diethylamino-6,7,8,9-tetrahydro-5H-benzocyclohepten-5-ol and 27.0 g of (S)-(+)-mandelic acid are dissolved in ethyl acetate and the precipitated crystals are recrystallized from ethyl acetate to obtain 26.1 g of (+)-trans-3-fluoro-5-(2-thienyl)-7-diethylamino-6,7,8,9-tetrahydro-5H-benzocyclohepten-5-ol.(S)-(+)-mandelate.

Yield: 30%
m.p.: 168°–170° C.
$[\alpha]_D^{20}$: $+64.0°$ (c=1.0, methanol)

(1)-(b) The above-obtained product is treated in the same manner as described in example 15-(1)-(b) to obtain (+)-trans-3-fluoro-5-(2-thienyl)-7-diethylamino-6,7,8,9-tetrahydro-5-H-benzocyclohepten-5-ol as an oil.
$[\alpha]_D^{20}$: $+64.0°$ (c=1.0, chloroform)

½ Fumarate of the product:
m.p.: 174°–176° C. (dec.) (recrystallized from isopropyl alcohol)
$[\alpha]_D^{20}$: $+45.9°$ (c=1.0, methanol)

(2)-(a) A mixture of n-hexane and an aqueous sodium bicarbonate solution is added to the mother liquor which is obtained after isolating (+)-trans-3-fluoro-5-(2-thienyl)-7-diethylamino-6,7,8,9-tetrahydro-5H-benzocyclohepten-5-ol.(S)-(+)-mandelate. The organic layer is washed, dried and condensed. The residue and 15.4 g of (R)-(−)-mandelic acid are treated in the same manner as described in example 15-(1)-(a) to obtain 30.9 g of (−)-trans-3-fluoro-5-(2-thienyl)-7-diethylamino-6,7,8,9-tetrahydro-5H-benzocyclohepten-5-ol.(R)-(−)-mandelate.

Yield: 36%
m.p.: 168°–169° C.
$[\alpha]_D^{20}$: $-63.8°$ (c=1.0, methanol)

(2)-(b) The above-obtained product is treated in the same manner as described in example 15-(1)-(b) to obtain (−)-trans-3-fluoro-5-(2-thienyl)-7-diethylamino-6,7,8,9-tetrahydro-5H-benzocyclohepten-5-ol as an oil.
$[\alpha]_D^{20}$: $-62.9°$ (c=1.0, chloroform)

½ Fumarate of the product:
m.p.: 174°–175° C. (dec.) (recrystallized from isopropanol)
$[\alpha]_D^{20}$: $-46.4°$ (c=1.0, methanol)

EXAMPLE 19

(1)-(a) 1.81 g of (S)-(+)-mandelic acid are dissolved in a solution of 3.89 g of (±)-cis-5-(2-thienyl)-7-(1-piperidinyl)-6,7,8,9-tetrahydro-5H-benzocyclohepten-5-ol in ethanol under heating and the precipitate is collected by filtration to obtain 1.69 g of (−)-cis-5-(2-thienyl)-7-(1-piperidinyl)-6,7,8,9-tetrahydro-5H-benzocyclohepten-5-ol.(S)-(+)-mandelate.
m.p.: 171.5°–173° C.

(1)-(b) The above-obtained product is treated in the same manner as described in example 15-(1)-(b) to obtain 1.16 g of (−)-cis-5-(2-thienyl)-7-(1-piperidinyl)-6,7,8,9-tetrahydro-5H-benzocyclohepten-5-ol as a caramel. $[\alpha]_D^{20}$: $-69.8°$ (c=1.0, chloroform)

Fumarate of the product:
m.p.: 171.5°–172.5° C. (dec.) (recrystallized from a mixture of ethanol and ether)
$[\alpha]_D^{20}$: $-51.9°$ (c=1.0, methanol)

(2) A mother liquor which is obtained after isolating (−)-cis-5-(2-thienyl)-7-(1-piperidinyl)-6,7,8,9-tetrahydro-5H-benzocyclohepten-5-ol.(S)-(+)-mandelate is treated with an aqueous sodium bicarbonate solution, and the mixture and (R)-(−)-mandelic acid are treated in the same manner as described in example 15-(1)-(a) to obtain 1.16 g of (+)-cis-5-(2-thienyl)-7-(1-piperidinyl)-6,7,8,9-tetrahydro-5H-benzocyclohepten-5-ol as a caramel.
$[\alpha]_D^{20}$: $+69.5°$ (c=1.0, chloroform)

Fumarate of the product:
m.p.: 171.5°–172.5° C. (dec.) (recrystallized from a mixture of ethanol and ether)
$[\alpha]_D^{20}$: $+51.5°$ (c=1.0, methanol)

EXAMPLE 20

A mixture of 0.362 g of potassium carbonate and 0.170 g of allyl bromide is added to a solution of 0.283 g of cis-5-(2-thienyl)-7-isopropylamino-6,7,8,9-tetrahydro-5H-benzocyclohepten-5-ol in 4 ml of dimethylformamide at room temperature and the mixture is stirred at the same temperature for 24 hours. An aqueous saturated sodium bicarbonate solution is added thereto and the mixture is extracted with ethyl acetate. The ethyl acetate layer is washed, dried and evaporated to remove the solvent. The residue is purified by silica gel column chromatography (solvent; chloroform:methanol=20:1) to obtain 0.320 g of cis-5-(2-thienyl)-7-(N-allyl-N-isopropylamino)-6,7,8,9-tetrahydro-5H-benzocyclohepten-5-ol as an oil.

IR (Film) cm$^{-1}$: 3400, 1670
Mass (m/z): 341(M$^+$)

½ Fumarate of the product:
m.p.: 177.0°–179.5° C. (dec.) (recrystallized from a mixture of ethanol and ether)

REFERENCE EXAMPLE 1

(1) 68.9 g of bromine are added dropwise to a solution of 73.1 g of 3-fluoro-6,7,8,9-tetrahydro-5H-benzocyclohepten-5-one in 700 ml of ether under ice-cooling during 1 hour. After the mixture is stirred for 1 hour, the reaction mixture is poured into water and the mixture is extracted with ether. The ether layer is washed, dried and evaporated to remove the solvent to obtain 106.8 g of 3-fluoro-6-bromo-6,7,8,9-tetrahydro-5H-benzocyclohepten-5-one as an oil.

IR (Neat) cm$^{-1}$: 1690
Mass (m/z): 258, 256(M$^+$)

(2) A mixture of 106.8 g of the above-obtained product, 108.2 g of lithium bromide, 107.4 g of lithium carbonate and 1 liter of dimethylformamide is stirred at 100° C. for 3 hours. The reaction mixture is poured into water and the mixture is extracted with ethyl acetate. The ethyl acetate layer is washed, dried and evaporated to remove the solvent to obtain 74.4 g of 3-fluoro-8,9-dihydro-5H-benzocyclohepten-5-one as an oil.

IR (Neat) cm$^{-1}$: 1645
Mass (m/z): 176(M$^+$)

(3) A mixture of 74.4 g of the above-obtained product, 370 ml of diethylamine and 79.2 g of p-toluenesulfonic acid.hydrate is stirred at a temperature from 0° C.

to room temperature for 16 hours. Ethyl acetate is added thereto and the mixture is extracted with 10% hydrochloric acid. After the aqueous layer is washed with ethyl acetate, the aqueous layer is treated with an aqueous potassium carbonate solution and extracted with ethyl acetate. The ethyl acetate layer is washed, dried and evaporated to remove the solvent to obtain 59.8 g of 3-fluoro-7-diethylamino-6,7,8,9-tetrahydro-5H-benzocyclohepten-5-one as an oil.

IR (Neat) cm$^{-1}$: 1680

Mass (m/z): 249(M$^+$)

REFERENCE EXAMPLE 2 TO 11

The corresponding starting compounds are treated in the same manner as described in Reference Example 1 to obtain the compounds listed in Table 4.

TABLE 4

| Ref Ex Nos. | R$^1$ | $-N\overset{R^2}{\underset{R^3}{\diagdown}}$ | Physicochemical Properties (Recrystallization Solvent) |
|---|---|---|---|
| 2 | —H | —N(C$_2$H$_5$)$_2$ | oil<br>MASS(m/z):231(M$^+$)<br>IR$^{Neat}_{\nu max}$(cm$^{-1}$):1670 |
| 3 | —OCH$_3$ | —N(C$_2$H$_5$)$_2$ | oil<br>MASS(m/z):261(M$^+$)<br>IR$^{Neat}_{\nu max}$(cm$^{-1}$):1670 |
| 4 | —H | —N(CH$_3$)$_2$ | oil<br>MASS(m/z):203(M$^+$)<br>IR$^{Neat}_{\nu max}$(cm$^{-1}$):1675 |
| 5 | —F | —N(CH$_3$)$_2$ | oil<br>MASS(m/z):221(M$^+$)<br>IR$^{Neat}_{\nu max}$(cm$^{-1}$):1680 |
| 6 | —H | —NHC(CH$_3$)$_3$ | Hydrochloride<br>m.p. 167-167.5° C.<br>(Ethanol-Ether) |
| 7 | —F | —NHC(CH$_3$)$_3$ | oil<br>MASS(m/z):249(M$^+$)<br>IR$^{Neat}_{\nu max}$(cm$^{-1}$):1680 |
| 8 | —H | —NHCH(CH$_3$)$_2$ | oil<br>MASS(m/z):217(M$^+$)<br>IR$^{Neat}_{\nu max}$(cm$^{-1}$):1675 |
| 9 | —H | 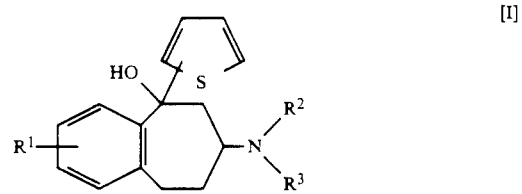 | oil<br>MASS(m/z):243(M$^+$)<br>IR$^{Neat}_{\nu max}$(cm$^{-1}$):1675 |
| 10 | —F | piperidinyl | m.p. 67-69.5° C.<br>(n-Hexane) |
| 11 | —OCH$_3$ | piperidinyl | m.p. 80-83° C.<br>(n-Hexane) |

What is claimed is:

1. A benzocycloheptene compound of the formula [I]:

wherein R$^1$ is hydrogen atom, a halogen atom or a lower alkoxy group, R$^2$ and R$^3$ combine together with adjacent nitrogen atom to form a heteromonocyclic group, or a pharmaceutically acceptable salt thereof.

2. The compound according to claim 1, wherein R$^1$ is substituted at the 3-position of the benzocycloheptene ring.

3. The compound according to claim 1, wherein R$^1$ is hydrogen atom, R$^2$ and R$^3$ combine together with adjacent nitrogen atom to form piperidinyl group or pyrrolidinyl group.

4. A cis isomer of the compound claimed in any of claims 1 to 3.

5. Cis-5-(2-thienyl)-7-(1-pyrrolidinyl)-6,7,8,9-tetrahydro-5H-benzocyclohepten-5-ol or a pharmaceutically acceptable salt thereof.

6. Cis-5-(2-thienyl)-7-(1-piperidinyl)-6,7,8,9-tetrahydro-5H-benzocyclohepten-5-ol or a pharmaceutically acceptable salt thereof.

7. A (+)-cis isomer of the compound claimed in claim 5 or 6.

8. A pharmaceutical composition which comprises a therapeutically effective amount of the compound as set forth in claim 1 in admixture with a conventional pharmaceutically acceptable carrier or diluent.

9. A method for the prophylaxis or treatment of pollakiuria, nocturia, enuresis or irritable bladder in a warm-blooded animal, which comprises administering to a warm-blooded animal a therapeutically effective amount of the compound as set forth in claim 1.